United States Patent [19]

Yokoshima et al.

[11] Patent Number: 4,889,768

[45] Date of Patent: Dec. 26, 1989

[54] NOVEL SILICON-URETHANE (METH) ACRYLATE, AND RESIN COMPOSITION AND COATING MATERIAL COMPRISING SAME

[75] Inventors: Minoru Yokoshima, Toride; Tetsuo Ohkubo, Ube, both of Japan

[73] Assignee: Nippon Kayaku Kabushiki Kaisha, Tokyo, Japan

[21] Appl. No.: 38,154

[22] Filed: Apr. 14, 1987

[30] Foreign Application Priority Data

Apr. 24, 1986 [JP] Japan .................... 61-93265

[51] Int. Cl.⁴ .............................. B32B 9/00
[52] U.S. Cl. .................... 428/429; 428/447;
522/90; 522/91; 522/99; 526/279; 427/180;
427/387; 556/414; 556/420; 556/425; 528/26;
528/41; 525/28; 525/29; 525/100; 525/101;
525/102; 525/470; 525/479; 525/278
[58] Field of Search ............... 556/414, 420, 425;
528/26, 41; 525/28, 29, 278, 100, 101, 102, 476,
479; 428/447, 429; 526/279; 427/180, 387;
522/90, 91, 99

[56] References Cited

U.S. PATENT DOCUMENTS 4,146,585  3/1979  Ward et al. .................... 525/104
4,491,650  1/1985  Rizk et al. .................... 525/102

FOREIGN PATENT DOCUMENTS 111280   6/1984  European Pat. Off. .
149741   7/1985  European Pat. Off. .
170154   9/1984  Japan .
118759   6/1985  Japan .
WO84/00969  3/1984  World Int. Prop. O. .

OTHER PUBLICATIONS

Eaborn, Organosilicon Compounds, Academic Press, Inc., New York, pp. 454–455 (1960).

Primary Examiner—Melvyn I Marquis
Attorney, Agent, or Firm—Banner, Birch, McKie & Beckett

[57] ABSTRACT

A silicon-urethane (meth) acrylate which is a reaction product of an isocyanato-alkylsilane compound represented by the following general formula:

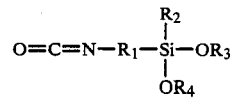

wherein $R_1$ represents an alkylene group having 2 to 5 carbon atoms, $R_2$ represents an alkyl group having 1 to 5 carbon atoms or alkoxy group having 1 to 5 carbon atoms, and $R_3$ and $R_4$ each represents an alkyl group having 1 to 5 carbon atoms, and a hydroxyl group-containing ester of (meth) acrylic acid, a resin composition and a coating material for optical glass fiber comprising said silicon-urethane (meth) acrylate.

14 Claims, No Drawings

NOVEL SILICON-URETHANE (METH) ACRYLATE, AND RESIN COMPOSITION AND COATING MATERIAL COMPRISING SAME

BACKGROUND OF THE INVENTION

1. Field of the Invention

The present invention relates to a novel silicon-urethane (meth)acrylate, as well as to a resin composition and a coating material for optical fiber comprising said silicon-urethane (meth)acrylate which is useful particularly as an ultraviolet-curable coating material to be applied to glass surface of optical fiber to protect it.

2. Description of the Prior Art

Since optical fiber has a high information-transmitting performance and it is relatively insusceptible to the external interference, its use has markedly increased in the later several years particularly in the field of communications. Optical fibers are generally made of glass, because they are used in the field of communications. However, glass fiber is fragile in its nature and can be chemically deteriorated by steam, so that it is readily breakable and difficult to handle. Accordingly, it has hitherto been conventional to coat glass fibers with a resin. As the resin for coating glass fibers, epoxy resin, urethane resin and the like have so far been used. However, these resins are disadvantageous in that they are inferior in productivity because their cure takes a long period of time and they are poor in flexibility so that transmitting performance of glass fiber can be deteriorated by lateral pressure. With the aim of overcoming the above-mentioned disadvantages, ultraviolet-curable compositions comprising urethane acrylate have energetically been studied recently, and ultraviolet-curable composition for optical glass fiber and a method for forming its coating film have been proposed in, for example, Japanese Patent Kokai (Laid-Open) No. 223,638/83 and EP 111,280.

Further, with the aim of improving the adhesion to glass, an ultraviolet-curable coating material for optical glass has been proposed in EP 149,741.

According to EP 149,741, polyalkoxysilane having one amino group or mercapto group is added to improve adhesion to glass. However, this composition has a problem that viscosity of the liquid can increase and gelation can take place, though the composition is excellent in adhesion to glass.

SUMMARY OF THE INVENTION

The present inventors conducted earnest studies with the aim of solving the above-mentioned problems. As the result, they succeeded in providing a resin composition excellent in adhesive property to glass, good in the stability as a composition and particularly suitable for use as a coating material for optical glass fiber for optical transmission. Based on this success, the present invention was accomplished. Thus, the present invention relates to:

(1) a silicon-urethane (meth)acrylate which is a reaction product of an isocyanato-alkylsilane compound represented by the following general formula (A):

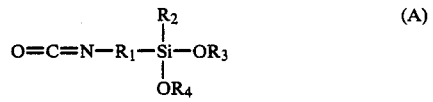

wherein $R_1$ represents an alkylene group having 2 to 5 carbon atoms and preferably 3 carbon atoms, $R_2$ represents an alkyl group having 1 to 5 carbon atoms or an alkoxy group having 1 to 5 carbon atoms and preferably an alkyl group having 1 to 3 carbon atoms or an alkoxy group having 1 to 3 carbon atoms, and $R_3$ and $R_4$ each represents an alkyl group having 1 to 5 carbon atoms and preferably 1 to 3 carbon atoms, and a hydroxyl group-containing ester of (meth)acrylic acid;

(2) a resin composition comprising a silicon-urethane (meth)acrylate which is a reaction product of a compound represented by the above-mentioned general formula (A) and a hydroxyl group-containing ester of (meth)acrylic acid; and (3) a coating material for optical glass fiber containing a silicon-urethane (meth)acrylate which is a reaction product of a compound represented by the general formula (A) and a hydroxyl group-containing ester of (meth)acrylic acid.

As used in the present invention, the term "(meth)acrylic acid" means "acrylic acid or methacrylic acid", and the term "(meth)acrylate" means "acrylate or methacrylate".

DETAILED DESCRIPTION OF THE INVENTION

In the present invention, silicon-urethane (meth)acrylate is used.

This novel silicon-urethane (meth)acrylate can be produced by reacting the compound represented by general formula (A) with a hydroxyl group-containing ester of (meth)acrylic acid.

Among the compounds represented by general formula (A), particularly preferably are γ-isocyanatopropyl-triethoxysilane, γ-isocyanatopropyl-methyl-diethoxysilane and γ-isocyanatopropylmethyl-dimethoxysilane.

Examples of the hydroxyl group-containing ester of (meth)acrylic acid [hereinafter, referred to as "compound (I)"] used in the present invention include hydroxyethyl (meth)acrylate, hydroxypropyl (meth)acrylate, ε-caprolactone-β-hydroxyalkyl (meth)acrylate adduct (PLACCEL FA-1, PLACCEL FA-2, PLACCEL FM-1, etc., manufactured by DAICEL Kagaku Kogyo K.K.), polyethylene glycol mono(meth)acrylate, polypropylene glycol mono(meth)acrylate, hydroxybutyl (meth)acrylate, and the like. Among them, hydroxyethyl acrylate, hydroxypropyl acrylate and the like are particularly preferable. The temperature at which the compound represented by general formula (A) is reacted with compound (I) is preferably in the range from room temperature to 100° C., and particularly in the range from 50° C. to 90° C. Per one mole of the compound represented by general formula (A), compound (I) can be used in an amount of 1 to 2 moles and preferably 1 to 1.5 moles. This reaction can be carried out in the presence of a known catalyst such as tertiary amine, dibutyltin dilaurate, dioctyltin dilaurate and the like in order to accelerate the reaction between isocyanate group and hydroxyl group. Preferably, these catalysts are used in an amount of 10 ppm to 300 ppm in the reaction mixture. Further, it is preferable to add 50 ppm to 2,000 ppm of a polymerization inhibitor such as hydroquinone, hydroquinone monomethyl ether, methylhydroquinone, p-benzoquinone, phenothiazine and the like to the reaction mixture in order to prevent the gelformation caused by radical polymerization which can take place in the course of reaction. The silicon-urethane (meth)acrylate is used preferably in an amount of 0.5 to 10% by weight and particularly 1 to 5% by weight based on the resin composition or coating material. The resin composition or coating material may comprise various known ethylenically unsaturated compounds as a component other than the silicon-urethane (meth)acrylate. Concrete examples of said ethylenically unsaturated compound include polyurethane (meth)acrylates such as polyurethane (meth)acrylate of polyether polyol having ether residue in its molecule, polyurethane (meth)acrylate of carbonate polyol having carbonate residue, polyurethane (meth)acrylate of polyester polyol having ester residue, polyurethane (meth)acrylate having both ether residue and ester residue, and the like; epoxy (meth)acrylates such as (meth-)acrylate of Bisphenol A type epoxy resin, (meth)acrylate of Bisphenol F type epoxy resin, (meth)acrylate of urethane-modified epoxy resin of Bisphenol A, and the like; polyester (meth)acrylates such as (meth)acrylate of polyester-diol composed of a diol compound (e.g. ethylene glycol, propylene glycol, diethylene glycol, dipropylene glycol, 1,5-pentanediol, 1,6-hexanediol and the like) and a dibasic acid (e.g. succinic acid, adipic acid, phthalic acid, hexahydrophthalic acid, tetrahydrophthalic acid and the like), (meth)acrylate of lactone-modified polyester diol composed of a diol compound, a dibasic acid and $\epsilon$-caprolactone, and the like; polycarbonate (meth)acrylates such as (meth)acrylate of polycarbonate diol having 1,6-hexanediol as its diol component, and the like; as well as phenyloxy polyethoxy (meth)acrylate, phenyloxy polypropoxy (meth)acrylate, nonylphenyloxy polyethoxy (meth)acrylate, nonylphenyloxy polyporpoxy (meth)acrylate, polypropylene glycol mono(meth)acrylate, polyethylene glycol mono(meth)acrylate, (meth)acrylate of tetrahydrofurfuryl alcohol-$\epsilon$-caprolactone adduct (e.g. KAYARAD TC-110S, TC-120, etc. manufactured by Nippon Kayaku K.K.), (meth)acrylate of tetrahydrofurfuryl alcohol-propylene oxide adduct, $\epsilon$-caprolactone-$\beta$-hydroxyethyl (meth)acrylate adduct (PLACCEL FA-2, FM-2, etc., manufactured by DAICEL Kagaku Kogyo K.K.), and (meth)acrylic esters represented by the following general formula (B):

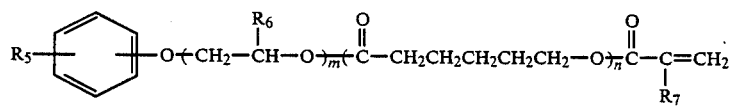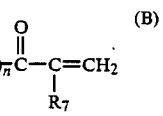

wherein $R_5$ represents a hydrogen atom or an alkyl group having 1 to 10 carbon atoms such as a nonyl group; $R_6$ and $R_7$ each represents hydrogen atom or a methyl group; mean value of m is 1 to 5; and mean value of n is 1 to 10.

Among them, particularly preferable ethylenically unsaturated compounds are polyurethane acrylate of polyether polyol, polyurethane acrylate of polycarbonate polyol, polyurethane acrylate of polyester polyol, nonylphenyloxy polyethoxy acrylate, nonylphenyloxy polypropoxy acrylate, acrylate of tetrahydrofurfuryl alcohol-$\epsilon$-caprolactone adduct, acrylate of nonylphenyloxy polyethoxy alcohol-$\epsilon$-caprolactone adduct, $\epsilon$-caprolactone-$\beta$-hydroxyethyl acrylate adduct, (meth-)acrylic esters represented by the above-mentioned general formula (B), and the like, for example. The above-mentioned ethylenically unsaturated compounds may be used either in the form of single compound or in the form of a mixture of two or more compounds having an arbitrary mixing ratio. Said ethylenically unsaturated compound is used preferably in an amount ranging from 80% to 99.4% by weight and particularly in an amount ranging from 90% to 97% by weight, based on the resin composition or coating material. These ethylenically unsaturated compounds are synthesizable according to the known method. Otherwise, they are readily available commercially. The resin composition or coating material of the present invention can be cured according to the known method. For example, they can be cured by means of ultraviolet ray. In the case of ultraviolet cure, a photopolymerization initiator must be used. As said photopolymerization initiator, any of the known photopolymerization initiators may be used, so long as it has a high storage stability after being compounded into the composition. Examples of such photopolymerization initiator include benzoin alkyl ethers such as benzoin ethyl ether, benzoin isobutyl ether, benzin isopropyl ether and the like; acetophenones such as 2,2-diethoxyacetophenone, 4'-phenoxy-2,2-dichloroacetophenone and the like; propiophenones such as 2-hydroxy-2-methylpropiophenone, 4'-isopropyl-2-hydroxy-2-methylpropiophenone, 4'-dodecyl-2-hydroxy-2-methylpropiophenone and the like; benzyl dimethyl ketal; 1-hydroxycyclohexyl phenyl ketone; anthraquinones such as 2-ethylanthraquinone, 2-chloroanthraquinone and the like; thioxanthones; and the like. Among them, particularly preferable are benzyl dimethyl ketal, 1-hydroxycyclohexyl phenyl ketone, and the like. These photopolymerization initiators may be used either in the form of single substance or in the form of a mixture of two or more members having an arbitrary mixing ratio. The photopolymerization initiator is used usually in an amount of 0.1 to 10% by weight and preferably 1 to 5% by weight, based on the weight of coating material.

If desired, modifying resin and various additives may be added to the resin composition and coating material of the present invention. As said modifying resin, epoxy resin, polyurethane, polybutadiene, polyether, polyamide-imide, silicone resin, phenolic resin and the like can be referred to. The modifying resin is used preferably in an amount ranging from 0% to 10% by weight and particularly in an amount ranging from 0% to 5% by weight, based on the resin composition or coating material.

As said additives, polymerization inhibitor (e.g. methoquinone, methylhydroquinone and the like), surfactant (e.g. SH-3749 manufactured by Toray Silicone K.K.), and the like can be referred to. Preferably, the polymerization inhibitor is used in an amount ranging from 0% to 1% by weight and the surfactant is used in an amount ranging from 0% to 3% by weight, both based on the weight of resin composition or coating material.

As the coating process for coating optical glass fiber with the coating material of the invention for glass fiber, dies coating process is preferable.

In coating a glass fiber with the coating material of the present invention for optical glass fiber, a base material of optical glass is linearly drawn at a speed of, for example, 1 to 5 m/second and it is coated with the coating material of the present invention, after which it is cured by ultraviolet irradiation and then coated with a top coating material.

The coating material of the present invention can easily be cured by ultraviolet irradiation. The cure of the coating material of the present invention by ultraviolet irradiation can be carried out in the usual way. For example, it is carried out by irradiating ultraviolet ray by means of low pressure mercury lamp, high pressure mercury lamp or xenon lamp.

The resin composition of the present invention is useful as a coating material for optical glass fiber. Further, it is also usable as a coating material for glass, an adhesive and a coating material for ceramics.

Next, the present invention will be illustrated more concretely with reference to the following non-limitative synthesis examples and examples. In the examples, "parts" means "parts by weight".

Syntheses of Ethylenically Unsaturated Compounds

Synthesis Example 1 (Polyurethane acrylate)

Into a 2 liter reactor equipped with a stirrer, a thermostat, a thermometer and a condenser were charged 500 parts of polycarbonate diol (DN-982 manufactured by Nippon Polyurethane K.K., molecular weight 2,000, hydroxyl number 56.0 mg KOH/g) and 83.3 parts of isophorone diisocyanate. After heating them to 80° C., they were reacted at this temperature for 10 hours, and the reaction mixture was cooled to 60° C. Then, 210 parts of ε-caprolactone-β-hydroxyethyl acrylate adduct (PLACCEL FA-2, manufactured by DAICEL Kagaku Kogyo K.K.), 0.4 part of methoquinone and 0.15 part of di-n-butyltin dilaurate were added, and the resulting mixture was heated and reacted at a temperature of 75° C. to 80° C. The reaction was continued until the concentration of free isocyanate group reached about 0.1% or below to indicate the completion of the reaction. The product had the following property.

Viscosity: 192 Poise (60° C.)

Syntheses of Silicon-Urethane (Meth)acrylates

EXAMPLE 1

Into a one liter reactor equipped with a stirrer, a thermostat, a thermometer and a condenser were charged 247 parts of γ-isocyanatopropyl-triethoxysilane (YH-9030, manufactured by Nippon Unicar Co., Ltd., NCO content 17.0%), 115 parts of 2-hydroxyethyl acrylate and 0.36 part of methoquinone. After heating the mixture to 80° C., it was reacted at that temperature until the concentration of free isocyanate group reached about 0.1% or below to indicate the completion of the reaction. Properties of the product were as follows:

Viscosity (25° C.): 62 cps
Acid value: 0.01 mg KOH/g

As measured by high resolution nuclear magnetic resonance (NMR), the frequency of the absorption of the product thus obtained was as follows:

| Results of NMR Measurement | | | |
|---|---|---|---|
| No. | Frequency of absorption (Hz) | No. | Frequency of absorption (Hz) |
| 1 | 2492.187 | 9 | 939.453 |
| 2 | 2347.656 | 10 | 878.906 |
| 3 | 1968.750 | 11 | 654.296 |
| 4 | 1927.734 | 12 | 351.562 |
| 5 | 1191.406 | 13 | 275.390 |
| 6 | 1160.156 | 14 | 115.234 |
| 7 | 1128.906 | 15 | 0.000 |
| 8 | 945.312 | | |

In the above-mentioned NMR measurement, tetramethylsilane was used as the standard substance. The measurement was conducted first by $^1$H and $^{13}$C-H coupling and finally by $^{13}$C-D coupling to obtain identification results.

EXAMPLE 2

Into the same reactor as in Example 1 were charged 247 parts of γ-isocyanatopropyl-triethoxysilane, 134 parts of 2-hydroxypropyl acrylate and 0.38 part of methoquinone. The mixture was heated to 80° C. and reacted at this temperature in the same manner as in Example 1 until the completion of the reaction. Properties of the product were as follows.

Viscosity (25° C.): 67 cps
Acid value: 0.02 mg KOH/g

| Results of NMR measurement | | | |
|---|---|---|---|
| No. | Frequency of absorption (Hz) | No. | Frequency of absorption (Hz) |
| 1 | 2492.187 | 12 | 1027.343 |
| 2 | 2343.750 | 13 | 1000.000 |
| 3 | 1968.750 | 14 | 878.906 |
| 4 | 1964.843 | 15 | 654.296 |
| 5 | 1933.593 | 16 | 349.609 |
| 6 | 1927.734 | 17 | 291.015 |
| 7 | 1193.359 | 18 | 275.390 |
| 8 | 1160.156 | 19 | 253.906 |
| 9 | 1128.906 | 20 | 246.093 |
| 10 | 1046.874 | 21 | 115.234 |
| 11 | 1037.109 | 22 | 0.000 |

EXAMPLE 3

Into the same reactor as in Example 1 were charged 247 parts of γ-isocyanatopropyl-triethoxysilane, 134 parts of 2-hydroxyethyl methacrylate and 0.19 part of methoquinone. The mixture was reacted in the same manner as in Example 1 until the completion of the reaction. Properties of the product were as follows.

Viscosity (25° C.): 60 cps
Acid value: 0.01 mg KOH/g

| Results of NMR measurement | | | |
|---|---|---|---|
| No. | Frequency of absorption (Hz) | No. | Frequency of absorption (Hz) |
| 1 | 2511.718 | 10 | 939.453 |
| 2 | 2349.609 | 11 | 916.015 |
| 3 | 2046.875 | 12 | 878.906 |
| 4 | 1890.625 | 13 | 656.250 |
| 5 | 1195.312 | 14 | 351.562 |
| 6 | 1164.062 | 15 | 275.390 |
| 7 | 1130.859 | 16 | 117.187 |
| 8 | 998.046 | 17 | 0.000 |
| 9 | 949.218 | | |

EXAMPLE 4

Into the same reactor as in Example 1 were charged 247 parts of γ-isocyanatopropyl-triethoxysilane, 354 parts of ε-caprolactone-β-hydroxyethyl acrylate adduct (PLACCEL FA-2, manufactured by DAICEL Kagaku Kogyo K.K.) and 0.3 part of methoquinone. In the same manner as in Example 1, the mixture was reacted until the completion of the reaction. Properties of the product were as shown below.

Viscosity (25° C.): 212 cps
Acid value: 0.03 mg KOH/g

Results of NMR measurement

| No. | Frequency of absorption (Hz) | No. | Frequency of absorption (Hz) |
|---|---|---|---|
| 1 | 2605.468 | 13 | 876.953 |
| 2 | 2490.234 | 14 | 654.296 |
| 3 | 2357.421 | 15 | 511.718 |
| 4 | 2349.609 | 16 | 433.593 |
| 5 | 1972.656 | 17 | 427.734 |
| 6 | 1925.781 | 18 | 384.765 |
| 7 | 1199.218 | 19 | 369.140 |
| 8 | 1166.615 | 20 | 351.562 |
| 9 | 1134.765 | 21 | 275.396 |
| 10 | 962.890 | 22 | 115.234 |
| 11 | 945.312 | 23 | 0.000 |
| 12 | 937.500 | | |

EXAMPLE 5

Into the same reactor as in Example 1 were charged 644.8 parts of γ-isocyanatopropyl-methyl-diethoxysilane, 355.2 parts of 2-hydroxyethyl acrylate and 1.0 part of methoquinone. In the same manner as in Example 1, the mixture was reacted until completion of the reaction. Properties of the product were as shown below.

Viscosity (25° C.): 99 cps
Acid value: 0.01 mg KOH/g

Results of NMR measurement

| No. | Frequency of absorption (Hz) | No. | Frequency of absorption (Hz) |
|---|---|---|---|
| 1 | 2492.187 | 14 | 910.156 |
| 2 | 2357.421 | 15 | 875.000 |
| 3 | 2345.703 | 16 | 656.250 |
| 4 | 1970.703 | 17 | 353.515 |
| 5 | 1927.734 | 18 | 306.640 |
| 6 | 1195.312 | 19 | 277.343 |
| 7 | 1162.109 | 20 | 253.906 |
| 8 | 1130.859 | 21 | 248.046 |
| 9 | 1070.312 | 22 | 222.656 |
| 10 | 1041.015 | 23 | 173.828 |
| 11 | 1029.296 | 24 | 169.921 |
| 12 | 1000.000 | 25 | −72.265 |
| 13 | 978.515 | | |

EXAMPLE 6

Into the same reactor as in Example 1 were charged 618.3 parts of γ-isocyanatopropyl-methyl-diethoxysilane, 381.7 parts of 2-hydroxypropyl acrylate and 1.0 part of methoquinone. In the same manner as in Example 1, the mixture was reacted until the completion of the reaction. Properties of the product were as shown below.

Viscosity (25° C.): 100 cps
Acid value: 0.02 mg KOH/g

Results of NMR measurement

| No. | Frequency of absorption (Hz) | No. | Frequency of absorption (Hz) |
|---|---|---|---|
| 1 | 2498.046 | 11 | 939.453 |
| 2 | 2359.375 | 12 | 912.109 |
| 3 | 2349.609 | 13 | 875.000 |
| 4 | 1970.703 | 14 | 656.250 |
| 5 | 1929.687 | 15 | 351.562 |
| 6 | 1193.359 | 16 | 277.343 |
| 7 | 1162.109 | 17 | 220.703 |
| 8 | 1128.906 | 18 | 167.968 |
| 9 | 986.328 | 19 | 0.000 |
| 10 | 945.312 | 20 | −74.218 |

EXAMPLE 7

In the same reactor as in Example 1 were charged 618.5 parts of γ-isocyanatopropyl-methyl-diethoxysilane, 381.5 parts of 2-hydroxyethyl methacrylate and 1.0 part of methoquinone. In the same manner as in Example 1, the mixture was reacted until the completion of the reaction. Properties of the product were as shown below.

Viscosity (25° C.): 90 cps
Acid value: 0.03 mg KOH/g

Results of NMR measurement

| No. | Frequency of absorption (Hz) | No. | Frequency of absorption (Hz) |
|---|---|---|---|
| 1 | 2607.421 | 14 | 656.250 |
| 2 | 2603.515 | 15 | 511.718 |
| 3 | 2492.187 | 16 | 484.375 |
| 4 | 2355.468 | 17 | 431.640 |
| 5 | 1972.656 | 18 | 425.781 |
| 6 | 1923.828 | 19 | 382.812 |
| 7 | 1193.359 | 20 | 369.140 |
| 8 | 1160.156 | 21 | 351.562 |
| 9 | 1128.906 | 22 | 275.390 |
| 10 | 962.890 | 23 | 220.703 |
| 11 | 935.546 | 24 | 166.015 |
| 12 | 931.640 | 25 | −74.218 |
| 13 | 873.046 | | |

EXAMPLE 8

Into the same reactor as in Example 1 were charged 379.9 parts of γ-isocyanatopropyl-methyl-diethoxysilane, 620.1 parts of ε-caprolactone-β-hydroxyethyl acrylate adduct (prepared by reacting 1 mole of 2-hydroxyethyl acrylate with 2 moles of ε-caprolactone; PLACCEL FA-2, manufactured by DAICEL Kagaku Kogyo K.K.) and 1.0 part of methoquinone. In the same manner as in Example 1, the mixture was reacted until the completion of the reaction. Properties of the product were as shown below.

Viscosity (25° C.): 245 cps
Acid value: 0.01 mg KOH/g

Results of NMR measurement

| No. | Frequency of absorption (Hz) | No. | Frequency of absorption (Hz) |
|---|---|---|---|
| 1 | 2515.625 | 11 | 937.500 |
| 2 | 2357.421 | 12 | 912.109 |
| 3 | 2349.609 | 13 | 875.000 |
| 4 | 2046.875 | 14 | 656.250 |
| 5 | 1888.671 | 15 | 351.562 |
| 6 | 1193.359 | 16 | 275.390 |
| 7 | 1160.156 | 17 | 220.703 |
| 8 | 1128.906 | 18 | 166.015 |
| 9 | 986.328 | 19 | 0.000 |

-continued

| Results of NMR measurement | | | |
|---|---|---|---|
| No. | Frequency of absorption (Hz) | No. | Frequency of absorption (Hz) |
| 10 | 947.265 | 20 | −76.171 |

EXAMPLE 9

Into the same reactor as in Example 1 were charged 612.6 parts of γ-isocyanatopropyl-methyl-dimethoxysilane, 387.4 parts of 2-hydroxyethyl acrylate and 1.0 part of methoquinone. In the same manner as in Example 1, the mixture was reacted until completion of the reaction. Properties of the product were as shown below.
Viscosity (25° C.): 105 cps
Acid value: 0.02 mg KOH/g

| Results of NMR measurement | | | |
|---|---|---|---|
| No. | Frequency of absorption (Hz) | No. | Frequency of absorption (Hz) |
| 1 | 2492.187 | 12 | 976.562 |
| 2 | 2343.750 | 13 | 779.296 |
| 3 | 1968.750 | 14 | 753.906 |
| 4 | 1925.781 | 15 | 656.250 |
| 5 | 1193.359 | 16 | 349.609 |
| 6 | 1160.156 | 17 | 304.687 |
| 7 | 1128.906 | 18 | 251.953 |
| 8 | 1068.359 | 19 | 244.140 |
| 9 | 1039.062 | 20 | 164.062 |
| 10 | 1027.343 | 21 | 154.296 |
| 11 | 998.046 | 22 | −89.843 |

Examples of Resin Composition (Coating Material)

EXAMPLE 10

Resin composition A (coating material) was prepared by mixing together 40 parts of the polyurethane acrylate prepared in Synthesis Example 1, 60 parts of acrylic ester of tetrahydrofurfuryl alcohol-ε-caprolactone adduct (KAYARAD TC-110S, manufactured by Nippon Kayaku K.K.), 2 parts of silicon-urethane acrylate prepared in Example 1, 5 parts of 1-hydroxycyclohexyl phenyl ketone (Irgacure 184, manufactured by Ciba-Geigy Ltd., photopolymerization initiator) and 0.01 part of methylhydroquinone.
Characteristics of the liquid composition and the cured product are summarized in Table 1.

EXAMPLE 11

Resin composition B (coating material) was prepared according to the formulation of Example 10, except that 2 parts of silicon-urethane acrylate used in the composition of Example 10 was replaced with 3 parts of silicon-urethane acrylate obtained in Example 2. Characteristics of the liquid composition and the cured product are summarized in Table 1.

EXAMPLE 12

Resin composition C (coating material) was prepared according to the formulation of Example 10, except that 2 parts of silicon-urethane acrylate used in the composition of Example 10 was replaced with 1 part of the silicon-urethane methacrylate obtained in Example 3. Characteristics of the liquid composition and the cured product are summarized in Table 1.

EXAMPLE 13

Resin composition D (coating material) was prepared according to the formulation of Example 10, except that 2 parts of silicon-urethane acrylate used in the composition of Example 10 was replaced with 2 parts of the silicon-urethane acrylate obtained in Example 4. Characteristics of the liquid composition and the cured product are summarised in Table 1.

EXAMPLE 14

Resin composition E was prepared according to the formulation of Example 10, except that 2 parts of silicon-urethane acrylate used in the composition of Example 10 was replaced with 2 parts of silicon-urethane acrylate obtained in Example 5. Characteristics of the liquid composition and the cured product are summarized in Table 1.

EXAMPLE 15

Resin composition F was prepared according to the formulation of Example 10, except that 2 parts of silicon-urethane acrylate used in the composition of Example 10 was replaced with 2 parts of the silicon-urethane acrylate obtained in Example 6. Characteristics of the liquid composition and the cured product are summarized in Table 1.

EXAMPLE 16

Resin composition G was prepared according to the formulation of Example 10, except that 2 parts of silicon-urethane acrylate used in the composition of Example 10 was replaced with 2 parts of the silicon-urethane methacrylate obtained in Example 7. Characteristics of the liquid composition and the cured product are summarized in Table 1.

EXAMPLE 17

Resin composition H was prepared according to the formulation of Example 10, except that 2 parts of silicon-urethane acrylate used in the composition of Example 10 was replaced with 2 parts of the silicon-urethane acrylate obtained in Example 8. Characteristics of the liquid composition and the cured product are summarized in Table 1.

EXAMPLE 18

Resin composition I was prepared according to the formulation of Example 10, except that 2 parts of silicon-urethane acrylate used in the composition of Example 10 was replaced with 2 parts of the silicon-urethane acrylate obtained in Example 9. Characteristics of the liquid composition and the cured product are summarized in Table 1.

Comparative Example 1

Resin composition J (coating material) was prepared according to the formulation of Example 10, except that 2 parts of silicon-urethane acrylate used in the composition of Example 10 was not used. Characteristics of the liquid composition and the cured product are summarized in Table 1.

Comparative Example 2

Resin composition K (coating material) was prepared according to the formulation of Example 10, except that 2 parts of silicon-urethane acrylate used in the composition of Example 10 was replaced with 2 parts of aminopropyl-trimethoxysilane. Characteristics of the liquid composition and the cured product are summarized in Table 1.

TABLE 1

| | Resin composition | | | | | | | | | | |
|---|---|---|---|---|---|---|---|---|---|---|---|
| | A | B | C | D | E | F | G | H | I | J | K |
| Adhesive strength to glass (g/cm) | 4.0 | 3.5 | 3.8 | 4.5 | 3.1 | 2.9 | 2.8 | 3.5 | 3.2 | 0.9 | 3.2 |
| Adhesive strength to glass (g/cm) (after moisture resistance test) | 4.1 | 3.4 | 3.9 | 4.6 | 3.0 | 2.9 | 2.9 | 3.5 | 3.1 | 0.9 | 3.3 |
| Stability of liquid composition | No abnormality | No abnormality | No abnormality | No abnormality | No abnormality | No abnormality | No abnormality | No abnormality | No abnormality | No abnormality | Gelation |

Notes to Table 1:
Measurement of adhesive strength to glass (g/cm): Each of the compositions A, B, C, D, E, F, G, H, I, J and K was coated on a glass plate and irradiated with a light source (a parallel arrangement of high pressure mercury lamps, output 2 KW/one lamp) by running the glass plate at a conveyer speed of 20 m/minute underneath the light source while keeping a distance of 8 cm from the light source. Thus, a cured film having a thickness of 250 μm was prepared. The cured film on the glass plate was cut into pieces having a width of 1 cm, and they were used for the measurement.
Measurement of adhesive strength to glass (g/cm) after moisture resistance test: A cured film on the glass plate was prepared in the same manner as in the above-mentioned measurement of adhesive strength (g/cm). After allowing the film to stand for 24 hours at a temperature of 25° C. at a humidity of 95% RH, it was used for the measurement:
Stability of liquid composition: A 100 g portion of each composition was taken into a brown-colored polyethylene bottle and allowed to stand for one month at a temperature of 60° C., after which its state was visually examined.

EXAMPLE 19

A base material of optical fiber was heated to about 2,000° C. and spun into an optical fiber having an outer diameter of 125 microns at a speed of 5 m/second. In the subsequent continuous steps, the glass fiber was coated with each of the resin compositions A to I of Examples 10 to 18 according to the dies coating process and cured by ultraviolet irradiation. Then, the primarily coated optical glass fiber thus obtained was top-coated (for example, with Desolite 950Y-100 manufactured by DeSoTo Ltd.) and cured by ultraviolet irradiation. The coated optical glass fiber thus obtained showed no change in the transmission loss down to the low temperature of −60° C., whichever of resin compositions A to I was used for the coating.

The resin composition of the present invention is excellent in adhesion to glass and stability in the state of liquid composition, and therefore it is particularly useful as a coating material for optical glass fibers used for optical transmissions.

What is claimed is:

1. A silicon-urethane (meth)acrylate which is a reaction product of an isocyanato-alkylsilane compound represented by the following general formula:

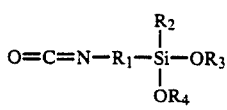

wherein $R_1$ represents an alkylene group having 2 to 5 carbon atoms, $R_2$ represents an alkyl group having 1 to 5 carbon atoms or alkoxy group having 1 to 5 carbon atoms, and $R_3$ and $R_4$ each represents an alkyl group having 1 to 5 carbon atoms, and a hydroxyl group-containing ester of (meth)acrylic acid.

2. A silicon-urethane (meth)acrylate according to claim 1, wherein $R_1$ represents an alkylene group having 3 carbon atoms, $R_2$ represents an alkyl group having 1 to 3 carbon atoms or alkoxy group having 1 to 3 carbon atoms, and $R_3$ and $R_4$ each represents an alkyl group having 1 to 3 carbon atoms.

3. A silicon-urethane (meth)acrylate according to claim 1, wherein said isocyanato-alkylsilane compound is γ-isocyanatopropyl-triethoxysilane, γ-isocyanatopropyl-methyl-diethoxysilane or γ-isocyanatopropyl-methyl-dimethoxysilane.

4. A silicon-urethane (meth)acrylate according to claim 1, 2 or 3, wherein said hydroxyl group-containing ester of (meth)acrylic acid is a compound selected from the group consisting of hydroxyethyl (meth)acrylate, hydroxypropyl (meth)acrylate, ε-caprolactone-β-hydroxyalkyl (meth)acrylate adduct, polyethylene glycol mono(meth)acrylate, polypropylene glycol mono(meth)acrylate and hydroxybutyl (meth)acrylate.

5. A composition comprising (1) 0.5% to 10% by weight of a silicon-urethane (meth)acrylate which is a reaction product of an isocyanato-alkylsilane compound represented by the following general formula:

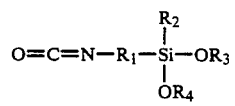

wherein $R_1$ represents an alkylene group having 2 to 5 carbon atoms, $R_2$ represents an alkyl group having 1 to 5 carbon atoms or alkoxy groups having 1 to 5 carbon atoms, and $R_3$ and $R_4$ each represents an alkyl group having 1 to 5 carbon atoms, and a hydroxyl group-containing ester of (meth)acrylic acid, (2) 80% to 99.4% by weight of an ethylenically unsaturated compound, wherein said ethylenically unsaturated compound is at least one compound selected from the group consisting of polyurethane (meth)acrylate, epoxy (meth)acrylate, polyester (meth)acrylate, polycarbonate (meth)acrylate, phenyloxypolyethoxy (meth)acrylate, phenyloxypolypropoxy (meth)acrylate, nonylphenyloxypolyethoxy (meth)acrylate, nonylphenyloxypolypropoxy (meth)acrylate, polypropylene glycol mono(meth)acrylate, polyethylene glycol mono(meth)acrylate, (meth)acrylate of tetrahydrofurfuryl alcohol-ε-caprolactone adduct, (meth)acrylate of tetrahydrofurfuryl alcohol-propylene oxide adduct, ε-caprolactone-β-hydroxyethyl (meth)acrylate adduct, and (meth)acrylic esters represented by the following general formula:

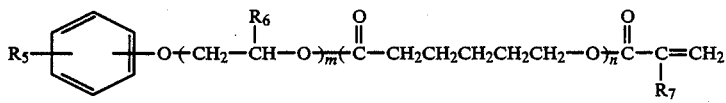

wherein $R_5$ represents a hydrogen atom or an alkyl group having 1 to 10 carbon atoms, $R_6$ and $R_7$ each represents a hydrogen atom or a methyl group, mean value of m is 1 to 5, and mean value of n is 1 to 10, and (3) 0.1% to 10% by weight of a photopolymerization initiator.

6. A composition according to claim 5, wherein said hydroxyl group-containing ester of (meth)acrylic acid is a compound selected from the group consisting of hydroxyethyl (meth)acrylate, hydroxypropyl (meth)acrylate, ε-caprolactone-β-hydroxyalkyl (meth)acrylate adduct, polyethylene glycol mono(meth)acrylate, polypropylene glycol mono(meth)acrylate and hydroxybutyl (meth)acrylate.

7. An optical glass fiber having a photopolymerized coating of the composition of claim 5.

8. An optical glass fiber having a photopolymerized coating of the composition of claim 6.

9. A silicon-urethane (meth)acrylate according to claim 1 wherein said reaction product is formed in the presence of a catalyst.

10. A silicon-urethane (meth)acrylate according to claim 1 wherein said reaction product is prepared in the presence of a polymerization inhibitor.

11. A silicon-urethane (meth)acrylate according to claim 10 wherein said polymerization inhibitor is selected from the group consisting of hydroquinone, hydroquinone monomethyl ether, methylhydroquinone, p-benzoquinone, and phenothiazine.

12. A composition according to claim 5 which contains a polymerization inhibitor.

13. A composition according to claim 5 wherein said reaction product is prepared in the presence of a polymerization inhibitor.

14. A composition according to claim 13 wherein said polymerization inhibitor is selected from the group consisting of hydroquinone, hydroquinone monomethyl ether, methylhydroquinone, p-benzoquinone, and phenothiazine.

* * * * *